United States Patent

Arquette

[11] Patent Number: 5,968,530
[45] Date of Patent: Oct. 19, 1999

[54] EMOLLIENT COMPOSITIONS

[75] Inventor: Demetrios James G. Arquette, Tempe, Ariz.

[73] Assignee: International Flora Technologies, Inc., Gilbert, Ariz.

[21] Appl. No.: 08/953,132

[22] Filed: Oct. 17, 1997

[51] Int. Cl.$^6$ .............................. A61K 7/00; A61K 7/42; A61K 7/021; A61K 7/025
[52] U.S. Cl. .............................. 424/401; 424/59; 424/63; 424/64; 424/502; 514/844; 514/873
[58] Field of Search ..................... 424/401, 502, 424/59, 63, 64; 514/844, 873

[56] References Cited

U.S. PATENT DOCUMENTS

| | | | |
|---|---|---|---|
| 1,944,887 | 1/1934 | Graves | 260/106 |
| 4,031,019 | 6/1977 | Bell | 252/56 S |
| 4,152,278 | 5/1979 | Bell | 252/56 S |
| 5,310,547 | 5/1994 | Dunphy et al. | 424/64 |
| 5,580,546 | 12/1996 | Ser et al. | 424/59 |
| 5,720,961 | 2/1998 | Fowler et al. | 424/401 |
| 5,814,311 | 9/1998 | Le Bras-Roulier et al. | 424/69 |

*Primary Examiner*—Shelley A. Dodson
*Assistant Examiner*—Marina Lamm
*Attorney, Agent, or Firm*—Schwegman, Lundberg, Woessner & Kluth PA

[57] ABSTRACT

An emollient composition is derived from jojoba oil comprises:

at least 10% by weight fatty alcohols comprising:

$$R^1CH_2-OH$$

at least 10% by weight of alkyl esters comprising:

$$R^1-COO-R_4$$

and wax esters selected from the group consisting of:

$$R^1-COO-CH_2-R^2$$

and $$R_2-COO-CH_2-R_1,$$

wherein $R^4$ comprises an alkyl or other aliphatic group, $R^1$ comprises $CH_3-(CH_2)_7-CH=CH-CH_2-(CH_2)_x-$, and $R^2$ comprises $CH_3-(CH_2)y$ wherein x is 6, 8, 10 and 12, and y is 16, 18, 20 and 22.

These emollient compositions may be used as emollient carriers for various materials to be externally applied to the skin.

16 Claims, No Drawings

EMOLLIENT COMPOSITIONS

EMOLLIENT COMPOSITIONS

This invention relates to emollient compositions for use in cosmetic, personal care and pharmaceutical preparations and more particularly to such emollient compositions and processes for their preparation.

BACKGROUND OF THE INVENTION

In the field of cosmetic, personal care, and pharmaceutical products emollients are usually defined as an agent that softens or smooths the skin and which tend to reduce the roughness, cracking and irritation of the skin. The ancient Greek physician, Galen, is thought to have made one of the first emollients consisting of beeswax, spermaceti, almond oil, borax and rosewater.

At the present, there are numerous ingredients which function as emollients in a wide variety of products, and which ingredients may act in subtly different ways. For example, certain emollients sit on the surface of the skin and serve to impede water loss from the skin. Such ingredients are generally comprise large molecules that forms a hydrophobic barrier to help prevent water from leaving the surface of the skin. Examples of such emollients are silicone derivatives and petroleum jelly.

Other ingredients that have been used as emollients include a number of fatty acids derived from either plants or animal sources. Fatty acids generally comprise aliphatic hydrocarbon or other organic chains with carboxylic substituents on them, typically having between 8 and 24 carbon atoms in the chain backbone. Fatty acids are often used in creams, lotions, shaving creams, lipsticks and as pressing agents in pressed powders and blushes. Fatty acids which are used in cosmetics formulations generally include at least stearic acid, oleic acid, myristic acid and palmitic acid. Other typical fatty acids include linoleic acid, behenic acid, and other common fatty acids of the general formula $C_nH_{2n+1}$ COOH.

Fatty alcohols are also used as emollients. They are said to be less sticky and less heavy than many other fatty materials, such as the fatty acids, and are frequently used to improve the viscosity and stability of lotions and creams. They also have utility in reactive hair dying and perming products. Examples of fatty alcohols which find use in the field of cosmetics and personal care products are cetyl alcohol, lauryl alcohol, stearyl alcohol and oleyl alcohol, and others of the general formula $C_nH_{2n+1}OH$.

Additional examples of emollients are fatty esters. One of the best qualities of fatty esters is that they do not feel as oily to the touch as some other types of emollient fatty ingredients. Examples include isopropyl palmitate, isopropyl myristate and glyceryl stearate.

An important emollient is jojoba oil which is derived from the seed of the species *Simmondsia chinensis*. It is a plant derived oil with excellent skin feel which is composed almost exclusively of wax esters, with little or no triglycerides present. A major portion of the production of jojoba oil is used by the cosmetic industry as an emollient in a variety of products. Although jojoba oil has long been used as an emollient, some difficulty has been found in forming stable emulsions using the oil.

The synthesis of esters and waxy esters of natural oils is known, as disclosed in U.S. Pat. Nos. 4,031,019 and 4,152,278 (the "Bell" patents), and this technology may be traced back to earlier seminal work done in U.S. Pat. No. 1,944,887. In the Bell patents, wax esters are prepared from acids obtained from hydrogenated vegetable oils. Fatty alcohols are esterified with the fatty acids to yield the wax esters which are described as useful for lubricants in replacement of sperm oil. U.S. Pat. No. 1,944,887 describes the manufacture of esters from monobasic saturated fatty acids containing 6 to 13 carbon atoms with aliphatic monohydric alcohols containing from 12 to eighteen carbon atoms.

SUMMARY OF THE INVENTION

The present invention describes a very effective emollient composition for use in personal care, cosmetic and pharmaceutical products and a novel method of producing that composition. The composition can be produced from a combinations of fatty alcohols, isopropyl esters and wax esters obtained from the oil contained in the seed of the jojoba plant (*Simmondsia chinensis*), jojoba oil.

These new emollient composition preserves the excellent skin feel attributed to jojoba oil, which has long been used as an emollient, and also increase the range of applications for cosmetic compositions by providing an emollient that can provide a more polar and hydrophilic quality than is found in jojoba oils, (which may also be referred to in the art as jojoba wax esters). The composition forms stable emulsions much more readily than does jojoba oil. The composition may also further provide excellent emolliency to normally dry cosmetic systems involving high levels of pigments, with the emollient acting as a pigment wetting agent. It also functions as an excipient in press powder.

The compositions comprising fatty alcohols, isopropyl esters and jojoba wax esters jojoba oil) may be obtained by the base catalyzed alcoholysis reaction between jojoba oil and isopropyl alcohol.

The fatty alcohol components of jojoba oil include a mixture of ingredients, but the largest segment of the oil comprises the fatty alcohols of the following general formula:

$$CH_3-(CH_2)_7-CH=CH-CH_2-(CH_2)_x-CH_2-OH$$

wherein X=6, 8, 10 and/or 12. The preferred fatty alcohols comprise those where X=8, 10 and/or 12.

Such fatty alcohols useful in our invention can be described as monounsaturated, straight chain, primary fatty alcohols (e.g., of 18 to 24 carbon atoms). A single double bond is located towards the middle of the respective fatty alcohol chain, specifically in the n−9 position (i.e., counted from the terminal (—CH$_3$) group). The preferred fatty alcohols are composed of even numbers of carbon atoms, specifically, 20 and 22 carbon atoms. The typical composition of the fatty alcohols used in this invention as determined by gas chromatography (GC) is:

| | FATTY ALCOHOLS | |
|---|---|---|
| X | (No. of carbon: No. of double bonds) | Typical % (area by GC) |
| 6 | 18:1 | 1 |
| 8 | 20:1 | 52 |
| 10 | 22:1 | 38 |

FATTY ALCOHOLS -continued

| X | (No. of carbon: No. of double bonds) | Typical % (area by GC) |
|---|---|---|
| 12 | 24:1 | 6 |
|  | other fatty alcohols | 3 |
|  | Total | 100 |

The isopropyl esters derived from jojoba oils according to a practice of this invention may have the following general formula:

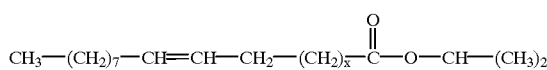

wherein X=6, 8, 10 and/or 12, preferably 8, 10 and/or 12.

Thus, the isopropyl esters useful in this invention are composed of monounsaturated, straight-chain fatty acids combined with isopropyl alcohol. The double bond is located in the middle of the respective fatty acid, specifically in the n–9 position. The fatty acids are all of even number of carbon atoms, primarily 20 and 22 carbons. The typical composition of the isopropyl esters found in this invention as determined by gas chromatography is:

| | Fatty Acid Component of Isopropyl Ester | |
|---|---|---|
| X | (No. of carbon atoms: No. of double bonds) | Typical % (area by GC) |
| 6 | 18:1 | 11 |
| 8 | 20:1 | 71 |
| 10 | 22:1 | 14 |
| 12 | 24:1 | 1 |
|  | trace isopropyl esters | 3 |

The jojoba wax esters which have been described in the present invention for use in the emollient composition can also be called randomized or interesterified jojoba esters. Such wax esters have the following general formula:

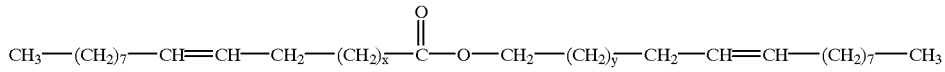

wherein X and Y are 6, 8, 10 or 12

The foregoing wax esters are composed of esters of straight chain monounsaturated fatty alcohols and monounsaturated fatty acids. A single double bond is located in the middle (n–9 position), counting from the terminal methyl group, (—CH$_3$) of the respective fatty acid and alcohol chain. Such wax esters are composed of fatty alcohols and fatty acids of even number of carbon atoms, primarily 20 and 22 carbons. The resulting esters have chain lengths of 38, 40, 42 and 44 with a small amount of esters of 36- and 46-carbon atoms being present. The typical composition of the wax esters is set out below.

WAX ESTERS

| (X, Y) | Wax Ester Chain Length | Typical (area by GC) |
|---|---|---|
| (6, 6) | 36 | 1 |
| (6, 8) (8, 6) | 38 | 8 |
| (6, 10) (8, 8) (10, 6) | 40 | 39 |
| (10, 8)(8, 10) | 42 | 38 |
| (10, 10) | 44 | 13 |
| (12, 10)(10, 12) | 46 | 1 |

The emollient compositions of the present invention comprise fatty alcohols, alkyl esters (including the isopropyl esters), and interesterified esters as described herein. The emollient composition should have a minimum of at least about 10% by weight of the foregoing fatty alcohols, at least 10% by weight of the foregoing isopropyl esters, with the balance preferably comprising interesterified jojoba esters, that is, the wax esters. Preferably the amount of each of the fatty alcohols and isopropyl esters will be from about 30–35% by weight of the composition, with the balance being the wax esters (with other emollient materials completing the balance). An especially preferred emollient composition will be as follows:

| Ingredient | % by weight |
|---|---|
| Fatty alcohols | 33 |
| Isopropyl esters | 33 |
| Wax esters | 33 |

Other emollients may be blended, mixed or dissolved with the basic emollient compositions described above.

DETAILED DESCRIPTION OF THE INVENTION

The present invention describes a very effective emollient composition for use in personal care, cosmetic and pharmaceutical products (especially topically applied pharmaceuticals) which can be produced from a combination of certain fatty alcohols, isopropyl esters and wax esters. More particularly, such components of the emollient composition can be obtained from the oil contained in the seed of the jojoba plant (*Simmondsia chinensis*), jojoba oil.

The new emollient composition may preserve the excellent skin feel attributed to jojoba oil, which has long been used as an emollient, but increases the range of application and types of ingredients which may be combined into a stable system with the emollient by providing an emollient that has a more polar and hydrophilic quality than is found in natural jojoba oils, also called jojoba wax esters. The composition forms stable emulsions much more readily than does jojoba oil and may further provide excellent emolliency to normally dry cosmetic systems involving high levels of pigments. It may also function as an excipient in pressed powders.

The seed of the jojoba plant contains about 50% by weight of an oil composed mainly of the straight chain monoesters of the $C_{20}$ and $C_{22}$ monoenoic alcohols and $C_{20}$ and $C_{22}$ monoenoic acids. The almost complete absence of glycerin in jojoba oil indicates that it is unique from all known seed oils in that it is not a triglyceride oil but a liquid wax. Jojoba oil, also known as jojoba wax esters, comprises materials which have the following general formula:

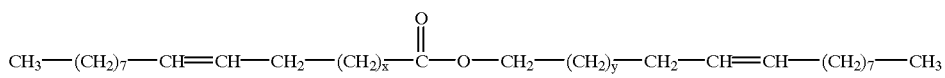

wherein X and Y are 6, 8, 10 or 12

The foregoing wax esters are composed of straight chain monounsaturated fatty alcohols and monounsaturated fatty acids. The single double bond is located towards the middle (n-9 position), counting from the terminal methyl group, ($-CH_3$) of the respective fatty acid or alcohol chain. Such wax esters are composed of fatty alcohols and fatty acids of even number of carbon atoms, primarily 20 and 22 carbons. The resulting esters have chain lengths of 38, 40, 42 and 44 with a small amount of esters of 36-carbon and 46-carbon atoms being present. The typical composition of the wax esters is set out below.

| WAX ESTERS | | |
|---|---|---|
| (X, Y) | Wax Ester Chain Length | Typical % (area by GC) |
| (6, 6) | 36 | 1 |
| (6, 8) (8, 6) | 38 | 8 |
| (6, 10) (8, 8) (10, 6) | 40 | 31 |
| (8, 10) (10, 8) | 42 | 49 |
| (10, 10) | 44 | 10 |
| (12, 10)(10, 12) | 46 | 1 |

The fatty alcohols and alkyl (e.g., C1 to C12, especially isopropyl) esters useful in this invention may be obtained by the base catalyzed alcoholysis reaction between the jojoba esters jojoba oil) and an appropriate aliphatic, e.g., appropriate alkyl alcohol, such as isopropyl alcohol. Thus the fatty alcohols useful in this invention have the following general formula:

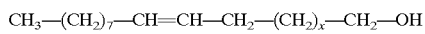

wherein X=6, 8, 10 and/or 12, preferably 8, 10 and 12.

The fatty alcohols useful in our invention are monounsaturated, straight chain, primary fatty alcohols. The single double bond is located approximately in the middle of the respective fatty alcohol chain, specifically in the n-9 position. The fatty alcohols are composed of even numbers of carbon atoms, specifically, 20 and 22. The typical composition of the fatty alcohols found in this invention is:

| FATTY ALCOHOLS | | |
|---|---|---|
| X | (No. of carbon: No. of double bonds) | Typical % (area by GC) |
| 6 | 18:1 | 1 |
| 8 | 20:1 | 52 |
| 10 | 22:1 | 38 |

| -continued | | |
|---|---|---|
| FATTY ALCOHOLS | | |
| X | (No. of carbon: No. of double bonds) | Typical % (area by GC) |
| 12 | 24:1 | 6 |
| | other fatty alcohols | 3 |

| -continued | | |
|---|---|---|
| FATTY ALCOHOLS | | |
| X | (No. of carbon: No. of double bonds) | Typical % (area by GC) |
| | Total | 100 |

The isopropyl esters typically found in this invention have the following general formula:

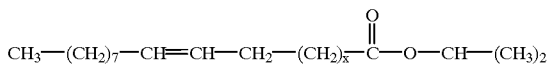

wherein X=6, 8, 10 and/or 12, preferably 6, 8 or 10

Thus, the isopropyl esters useful in this invention are composed of monounsaturated, straight chain fatty acids combined with isopropyl alcohol. The double bond is located in the middle of the respective fatty acid, specifically in the n-9 position. The fatty acids are all of even number of carbon atoms, primarily 20 and 22 carbons. The typical composition of the isopropyl esters found in this invention is:

| | Fatty Acid Component of Isopropyl Ester | |
|---|---|---|
| X | (No. carbon atoms: No. of double bonds) | Typical % (area by GC) |
| 6 | 18:1 | 11 |
| 8 | 20:1 | 71 |
| 10 | 22:1 | 14 |
| 12 | 24:1 | 1 |
| | trace isopropyl esters | 3 |

The emollient composition should have a minimum of at least about 10% by weight of the foregoing fatty alcohols, at least about 10% by weight of the foregoing isopropyl esters, preferably with the balance of the composition being jojoba esters, that is, the wax esters (although other emollient or inert or filler materials may be present in the emollient composition, not considering active or other functional materials). Preferably the amount of each of the fatty alcohols and isopropyl esters will be from about 30–35% by weight of the composition, with the balance being the wax esters. An especially preferred emollient composition is as follows:

| Ingredient | % by weight |
|---|---|
| Fatty alcohols | 33 |
| Isopropyl esters | 33 |
| Wax esters | 33 |

As the proportion of isopropyl esters and/or the fatty alcohols is increased, the emollient becomes more polar and of a lower viscosity, properties which should be very useful to the formulator. See the table immediately below.

Emollient Viscosity as a Function of Ester Content

| Wax Ester % | Fatty Alcohol & Isopropyl Ester | Viscosity, centipoise @ 25° C. |
|---|---|---|
| 100 | 0 | 41 |
| 75 | 25 | 28 |
| 50 | 50 | 22 |
| 25 | 75 | 20 |
| 10 | 90 | 17 |
| 0 | 100 | 17 |

One aspect of the present invention comprises emollient carrier compositions comprising:
 partially saturated wax esters comprising:
  (IV) $R^1$—COOO—$CH_2$—$R^2$ and/or (V) $R^2$—COOO—$CH_2$—$R^1$ at least 10% by weight of alkyl esters comprising:
  (VI) $R^1$—COOO—$R^4$ and/or (VII) $R^2$—COOO—$R^4$, and at least 10% by weight of fatty alcohols comprising:
  (VIII) $R^1CH_2$—OH and/or (IX) $R^2CH_2$—OH wherein $R^4$ comprises an alkyl or other aliphatic group (particularly $C_nH_{2n+1}OH$, where n=1 to 12), $R^1$ comprises

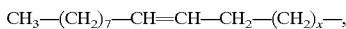

and
 $R^2$ comprises $CH_3$—$(CH_2)y$—
wherein x is 6,8 10 and/or 12, and y is 16, 18, 20 and/or 22. The term emollient carrier reflects the fact that the at least three materials described above (the partially saturated wax esters, the alkyl esters and the fatty alcohols) form a component which may be mixed, blended dispersed, emulsified or dissolved with other materials, is itself an emollient, and may be a carrier for these other materials. Typical additional materials which may be combined with the emollient carrier of the invention may include, but are not limited to, additional emollients, oils, fragrances, pigments (e.g., inorganic pigments, organic pigments, dyes), medicaments (e.g., antimicrobial agents, antibacterial materials, antifungal materials, anti-inflammatory agents, transcutaneously administered drugs, etc.), emulsifying agents, stabilizing agents, binders, fillers, antiagglomerants (especially where powders are present in the emollient carrier, as with certain cosmetics), ultraviolet radiation absorbers (as in the formulation of sunblocks and sunscreens), insect repellants (e.g., DEET), pheromones, enzymes, barrier materials (e.g., resins to prevent contact with toxins such as plant irritants), and the like. These materials may be present in essentially any desired amount, but usually within the range of from 0.1% by weight of total composition up to 99% by weight of total composition, with 0.1 to 50% by weight preferred, and 0.5% to 25% by weight being more preferred.

The fundamental reactions used in the practice of the present invention may be generally considered in the following manner. Starting materials could include:

I. The alcohol,
 $R^4$—OH (with isopropyl alcohol (IPA, HO—$CH_2$—$(CHC_3)_2$) being primarily emphasized),
II. Jojoba Wax Esters
 $R^1$—COO—$CH_2$—$R^1$, and
III. Fully hydrogenated Jojoba Wax Esters
 $R^2$—COO—$CH_2$—$R^2$
wherein $R^4$ is an alkyl group or other aliphatic group, preferably of 1 to 12 carbon atoms, more preferably an iso-alkyl group, and most preferably an isopropyl group,
 $R^1$ comprises $CH_3$—$(CH_2)_7$—CH=CH—$CH_2$—$(CH_2)_x$—, and
 $R^2$ comprises CH3—$(CH_2)y$—
wherein x is 6, 8, 10 and/or 12, and y is 16, 18, 20 and/or 22.
 $R^4$ comprises $C_nH_{2n+1}$—, wherein n=1 to 12.

Typical product components from the preferred synthetic reactions used in the practice of the present invention with jojoba oil may include:
 Partially saturated wax esters:
 IV. $R^1$—COO—$CH_2$—$R^2$ and/or V. $R^2$—COO—$CH_2$—$R^1$,
 (Where isopropyl alcohol was used) Iso-propyl esters
 VI. $R^1$—COO—CH—$(CH_3)_2$[generically $R^1$—COO—$R^4$] and/or
 VII. $R^2$—COO—CH—$(CH_3)_2$[generically $R^2$—COO—$R^4$] and
 Wax esters comprising
 VIII. $R^1CH_2$—OH and/or IX. $R^2CH_2$—OH.

The basic reactions which may be used in the preparation of the emollient compositions of the invention derived from jojoba oil may include at least the following procedures.

Reaction A I and IIn (catalyst)→VI, VIII and IIr. This product is referred to herein as "IPJ" and is a liquid.

Reaction B I and IIIn (catalyst)→VII, IX and IIIr. This product is referred to herein as "fully hydrogenated IPJ" or "HIPJ" and is a solid.

Reaction C I, and IIn and IIIn (catalyst)→IV, V, VI, VII, VIII, IX, IIr and IIIr. This product is referred to herein as "the broad melting range emollient" and the properties of the emolient depend upon the relative amounts of IIn and IIIn.

The subscripts n and r respectively represent n=the naturally occurring distribution of wax esters and r=the randomized distribution of wax esters resulting from rearrangements which occur during the reactions. It is to be noted that mixing of the reaction products from A and B will give emollients with a wide range of melting points, but will not be identical to the reaction product of C because of the absence of IV and V.

A process for producing an emollient may comprise the steps of:
 a) providing a composition comprising jojoba oil,
 b) adding an alcohol, e.g., having from 1 to 12 carbon atoms, to said composition,
 c) effecting alcoholysis on said jojoba oil mixed with said alcohol to produce an emollient, and
 d) effecting interesterification of remaining wax esters In preparing the emollient composition, refined jojoba oil (or hydrogenated jojoba oil or a mixture of the oil and hydrogenated oil) is introduced into an appropriate vessel (capable of excluding air) equipped with stirring and means of heating and cooling. The jojoba oil is first dried under vacuum at a temperature of 90 C. to remove most or all moisture. The anhydrous isopropyl alcohol (or other alcohol) is then added with the amount of isopropyl used being from about 20% to about 50% by weight of jojoba oil. The reactor is sealed and heat is applied to bring the temperature of the reaction mixture to about 70–75° C. It is important that air be excluded and that the reactor be vented through a condenser to recover any unreacted alcohol. When the temperature has reached 70–75° C., a first addition of catalyst (e.g., a catalyst for alcoholysis and interesterification such as sodium methoxide) is made. The amount added ranges from about 0.5% to about 0.6% by weight of the jojoba oil with about 0.3% being preferred. After about 2 hours, a sample is taken and analyzed for the presence of the wax esters. If the wax ester content is greater than about 25% by weight, and it is desired to have a lower level of wax esters present in the reaction mixture, a second addition of catalyst is made, about 0.1% by weight of the original amount of jojoba oil. The reaction is then continued for an additional one hour. The reaction mixture is then sampled and analyzed again. If the residual wax ester content is less than about 25–35%, the reaction may be considered to be complete. Heating is discontinued but no cooling is applied. If the reaction is considered incomplete, a third catalyst addition may be made and the reaction continued as previously described. Any remaining catalyst can be neutralized and deactivated by the addition of citric acid. After about 15 minutes of agitation the neutralized catalyst (sodium citrate) is removed by filtration. Once the catalyst has been removed, any remaining isopropyl alcohol can be distilled from the product and the recovered isopropyl alcohol should be kept absolutely dry in order to be able to be used again.

Following the previously described procedure, Examples I, II and III detail the preparation of three batches of emollient compositions.

EXAMPLE I

| Input Material | Weight kg |
|---|---|
| Refined jojoba oil | 99.90 |
| Isopropyl Alcohol | 24.80 |
| Catalyst (Na methoxide) | 0.43 |
| Filter Aid | 2.00 |
| Output Materials | |
| Emollient composition comprising jojoba esters, fatty alcohols and isopropyl esters | 99.4 |
| Recovered isopropyl alcohol | 13.0 |

The emollient composition was then bleached using 1% by weight of Clarion™ 470 bleaching clay supplied by American Colloid Company. The amount of bleached emollient composition obtained was 89.8 kg, a yield of about 90.8% based on the weight of the starting jojoba oil. After bleaching, the composition was deodorized followed by the addition of 0.5 kg. (500 ppm) of the antioxidant, Tenox GT-2, supplied by Eastman Chemical Company.

Analysis of the emollient composition by gas chromatograph gave the following results:

| | % |
|---|---|
| Fatty Alcohols (Chain Length) | |
| 20 | 14.6 |
| 22 | 15.0 |
| 24 | 3.3 |

| | % |
|---|---|
| Total Isopropyl Esters (Chain length) | 32.9 |
| 18 | 3.0 |
| 20 | 21.0 |
| 22 | 4.5 |
| 24 | 0.6 |
| Total Wax Esters (Chain length) | 29.1 |
| 38 | 3.2 |
| 40 | 15.6 |
| 42 | 12.9 |
| 44 | 4.8 |
| 46 | 0.6 |
| | 37.4 |

Observations

The reaction was run at 70–75 C. Starting with an amount of isopropyl alcohol equal to 25% of jojoba oil added, the reduction of wax esters became very slow after reaching 47%. Addition of more catalyst (0.1%), four hours after the initial addition, had only a slight effect of further reduction of wax esters. This product is liquid at room temperature.

| Time, hours | Comments |
|---|---|
| 0 | Addition of 0.3% catalyst, beginning of reaction, 100% wax esters |
| 2 | 46.9% residual wax esters |
| 3.5 | 42% residual wax esters |
| 4 | add 0.1% catalyst |
| 4.5 | 38% residual wax esters |
| 6 | add citric acid and end reaction |

EXAMPLE II

| Input Material | Weight kg |
|---|---|
| Refined jojoba oil | 101.00 |
| Isopropyl Alcohol | 46.50 |
| Catalyst (Na methoxide) | 0.30 |
| Filter Aid | 2.00 |
| Citric Acid | 0.25 |
| Output Materials | |
| Emollient composition comprising jojoba oil, fatty alcohols and isopropyl esters | 100.00 |
| Recovered isopropyl alcohol | 29.25 |

The foregoing composition was then bleached using 2.03% by weight of Clarion™ 470 bleaching clay supplied by American Colloid Company. The amount of bleached emollient composition obtained was 91.9 kg, a yield of about 91.4% based on the weight of the starting jojoba oil. After bleaching, the composition was deodorized followed by addition of 0.55 kg. of Tenox GT-2, supplied by Eastman Chemical Company.

Analysis of the composition by gas chromatograph gave the following results:

| Fatty Alcohols (Chain Length) | % |
|---|---|
| 20 | 17.2 |
| 22 | 15.7 |
| 24 | 3.1 |
| Total | 36.0 |
| Isopropyl Esters (Chain length) | |
| 18 | 4.2 |
| 20 | 25.8 |
| 22 | 4.9 |
| 24 | 0.5 |
| Total | 35.4 |
| Wax Esters (Chain length) | |
| 38 | 2.2 |
| 40 | 10.6 |
| 42 | 10.9 |
| 44 | 3.1 |
| 46 | 0.8 |
| | 27.6 |

Observations

This reaction was run at 80–85° C. Starting with an amount of isopropyl alcohol equal to 46% of jojoba oil added, the reduction of wax esters was accelerated. The residual wax ester content was approximately 28% after two hours with no additional catalyst being added. There was no change in the ester composition after an additional hour. The reaction was terminated by the addition of citric acid. The filtration of the sodium citrate proved difficult. There was a darker yellow color in this run as compared with example I. This was attributed to running the reaction at the higher temperature.

EXAMPLE III

| Imput Material | Weight, kg |
|---|---|
| Hydrogenated jojoba oil | 144 |
| Isopropyl alcohol | 72 |
| Catalyst (Na methoxide) | 0.576 |
| Citric acid | 0.36 |
| Output Materials | |
| Emollient composition comprising saturated jojoba ester; Saturated fatty alcohols and saturated isopropyl esters | 117.3 |
| Recovered isopropyl alcohol | 42 |

The foregoing composition was then bleach using 2% by weight Clarion 470 bleaching clay supplied by American Colloid Co. Following bleaching, the composition was deodorized. To the final product 0.08 kg of Tenox GT-2 supplied by Eastman Chemical Co. were added as an antioxidant. The yield was 81%.

Analysis of the emollient composition by gas chromatography gave the following results:

| Saturated Fatty Alcohols (Chain length) | Percent (%) |
|---|---|
| 20 | 17.2 |
| 22 | 17.2 |
| 24 | 3.4 |
| Total | 37.8 |
| Saturated Isopropyl Esters (Chain length) | |
| 18 | 4.0 |
| 20 | 24.5 |
| 22 | 4.8 |
| 24 | 3.4 |
| Total | 36.7 |
| Saturated Jojoba Esters (Chain length) | |
| 38 | 1.8 |
| 40 | 9.7 |
| 42 | 9.7 |
| 44 | 3.1 |
| 46 | 0.4 |
| Total | 24.7 |

Observations

This reaction was run at 70–74° C. for two hours. Starting with an amount of isopropyl alcohol equal to 50% of the hydrogenated jojoba oil added, the reduction of wax esters essentially complete when the residual wax esters reached 25%. The melting point of the product was 50–60° C.

To demonstrate the usefulness of the emollient compositions of this invention, the following examples show the preparation of a sun screen, eye cream, lipstick and foundation product. In each example, the product was prepared using an emollient composition of this invention and compared to the same product using a commercially available emollient.

EXAMPLE IV

Two (2) different lipsticks were prepared, one using an emollient composition of this invention; the other a conventional emollient, jojoba oil.

| | | Product | |
|---|---|---|---|
| Phase | Ingredient | III-A | III-B |
| A | Castor Oil | 41.0 | 41.0 |
| | Jojoba Oil | 15.0 | — |
| | Special Emollient* | — | 15.0 |
| | Jojoba Esters | 1.0 | 1.0 |
| | Carnauba Wax | 4.0 | 4.0 |
| | Candelilla Wax | 5.0 | 5.0 |
| | Beeswax | 3.5 | 3.5 |
| | Microcrystalline Wax | 4.0 | 4.0 |
| | Propylparaben | 0.1 | 0.1 |
| | Silica | 0.2 | 0.2 |
| B | Castor Oil | 13.0 | 13.0 |
| | Polyhydroxystearic Acid | 0.5 | 0.5 |
| | Titanium Dioxide | 5.5 | 5.5 |
| | Iron Oxides - Red 3511 | 4.0 | 4.0 |
| | D & C Red 30, Talc Lake | 2.5 | 2.5 |
| | FD & C Blue No. 1, Aluminum Lake | 0.1 | 0.1 |
| | Iron Oxides - Black 3070 | 0.5 | 0.5 |
| C | Tocopherol | 0.1 | 0.1 |
| | TOTAL | 100.0 | 100.0 |

*Emollient consisted of IPJ: 30% jojoba wax esters; 32% isopropyl esters; and 36% jojoba alcohols.

I. Combine ingredients of Phase A and heat to 85° C. with moderate agitation.
II. Combine Phase B and pass 2 times through a 3-roll mill. Add Phase B to Phase A with propeller agitation.
III. Cool batch to 75° C. add, Phase C and mix with propeller agitation. Fill as soon as possible.

Observations

In comparing products III-A and III-B, it was observed that product III-B, which contained an emollient composition of this invention, had a smoother application, better slip and more gloss than product III-A.

EXAMPLE V

Three different foundation creams were prepared, one using the emollient composition of this invention.

| Phase | Ingredient | IV-A | IV-B | IV-C |
|---|---|---|---|---|
| A | Water | 53.63 | 53.63 | 53.63 |
|   | Cellulose Gum | 0.30 | 0.30 | 0.30 |
|   | Magnesium Aluminum Silicate | 0.80 | 0.80 | 0.80 |
|   | Propylene Glycol | 10.00 | 10.00 | 10.00 |
| B | Talc | 3.00 | 3.00 | 3.00 |
|   | Titanium Dioxide | 11.00 | 11.00 | 11.00 |
|   | Iron Oxides - Red 3080 | 0.20 | 0.20 | 0.20 |
|   | Iron Oxides - Yellow 3170 | 1.14 | 1.14 | 1.14 |
|   | Iron Oxides - Red 3551 | 0.22 | 0.22 | 0.22 |
|   | Iron Oxides - Black 3070 | 0.28 | 0.28 | 0.28 |
| C | Disodium Oleamide PEG-2 Sulfosuccinate | 0.13 | 0.13 | 0.13 |
| D | Special Emollient* | 11.00 | — | — |
|   | Jojoba Esters | — | 11.00 | — |
|   | Isopropyl Palmitate | — | — | 11.00 |
|   | Tocopheryl Acetate | 0.20 | 0.20 | 0.20 |
|   | Cetyl Alcohol | 0.50 | 0.50 | 0.50 |
|   | Stearic Acid | 2.40 | 2.40 | 2.40 |
|   | Glyceryl Sterate & PEG-100 Stearate | 0.60 | 0.60 | 0.60 |
|   | Dimethicone | 0.20 | 0.20 | 0.20 |
|   | Cyclomethicone | 3.00 | 3.00 | 3.00 |
| E | Propylene Glycol & Diazolidinyl Urea (and) Methylparaben (and) Propylparaben | 1.00 | 1.00 | 1.00 |
|   | Triethanolamine | 0.40 | 0.40 | 0.40 |
|   | TOTAL | 100.00 | 100.00 | 100.00 |

*Emollient consisted of: IPJ 30% jojoba wax esters; 32% isopropyl esters; and 36% jojoba alcohols.

II. Heat water of Phase A to 75° C., Premix CMC and Veegum. Add CMC and Veegum to water with rapid propeller agitation. Mix for 30 minutes. Add propylene glycol to water with moderate agitation; mix for 10 minutes at 75° C.
III. Add pigments/talc of Phase B to Phase A at 75° C. with high speed homomixer agitation. Agitate for 30 minutes
IV. Add Phase C to Phase AB with moderate homomixer agitation. Mix 10 minutes and hold at 80° C.
V. Combine Phase D and heat to 80° C. with agitation. With Phase ABC and Phase D at 80° C., add Phase D slowly to Phase ABC with moderate propeller agitation. Mix 20 minutes and then force cool with agitation to 75° C.
VI. Add Phase E to batch at 75° C. and cool to room temperature with moderate propeller agitation.

Observations

The foregoing products are oil in water emulsions. It was observed that product IV-A, which contained an emollient composition of this invention, exhibited longer playtime, smoother application, and a richer, more moist feel than products IV-B and IV-C.

EXAMPLE VI

Two eye creams were prepared; one using the emollient composition of this invention.

| Phase | Ingredient | V-A | V-B |
|---|---|---|---|
| A | Water | 73.35 | 73.35 |
|   | Disodium EDTA | 0.05 | 0.05 |
|   | Carbomer | 0.30 | 0.30 |
|   | Methylparaben | 0.20 | 0.20 |
|   | Imidiazolidinyl Urea | 0.15 | 0.15 |
| B | Special Emollient* | 18.0 | — |
|   | Isopropyl Palmitate | — | 18.00 |
|   | Glyceryl Stearate & PEG-100 Stearate | 1.50 | 1.50 |
|   | Propylparaben | 0.10 | 0.10 |
|   | Polysorbate 60 | 2.20 | 2.20 |
|   | Sorbitan Stearate | 0.50 | 0.50 |
|   | Cetyl Alcohol | 1.10 | 1.10 |
|   | Stearic Acid | 0.50 | 0.50 |
|   | Tocopheryl Acetate | 0.20 | 0.20 |
| C | Triethanolamine | 0.35 | 0.35 |
| D | Acetamide MEA | 1.50 | 1.50 |
|   | TOTAL | 100.0 | 100.0 |

*Emollient consisted of: IPJ 30% jojoba wax esters; 32% isopropyl esters; and 36% jojoba alcohols.

II. Slowly sprinkle Carbopol of Phase A into cold water with rapid propeller agitation. Add remaining ingredients and heat Phase A to 80° with agitation.
III. Heat Phase B to 80° C. with agitation
IV. Add Phase B slowly to Phase A with moderate propeller agitation. Mix 10–15 minutes until mixture is uniform.
V. Add Phase C and Phase D to batch with moderate propeller agitation. Mix 10–15 minutes until mixture is uniform. Cool to room temperature.

Observations

These eye creams are oil in water emulsions. It was observed that product V-A exhibited less drying, was of a smoother consistency, longer playtime and easier to emulsify than product V-B.

EXAMPLE VII

Two sun screen preparations were made; one using isopropyl palmitate (IPP) and the other using the emollient of this invention in place of the IPP.

| Phase | Ingredient | VI-A | VI-B |
|---|---|---|---|
| A | Special Emollient* | 4.60 | — |
|   | Isopropyl Palmitate | — | 4.60 |
|   | Cetyl Dimethicone Copolyol | 2.00 | 2.00 |
|   | PPG-3 Myristyl Ester | 0.50 | 0.50 |
|   | Hydrogenated Caster Oil | 0.75 | 0.75 |
|   | Microcrystalline Wax | 1.25 | 1.25 |
|   | Cyclomethicone | 4.00 | 4.00 |
|   | Cetyl Dimethicone | 1.00 | 1.00 |
|   | Titanium Dioxide & Hybrid Sunflower (Helianthus Annuus) Oil | 3.00 | 3.00 |
| B | Octyl Methoxycinnamate | 4.50 | 4.50 |
|   | Benzophenone-3 | 2.50 | 2.50 |
|   | Octyl Palmitate | 5.50 | 5.50 |
| C | Water | 68.20 | 68.20 |
|   | Propylene Glycol | 0.40 | 0.40 |
|   | Sodium Chloride | 0.80 | 0.80 |

-continued

| Phase | Ingredient | VI-A | VI-B |
|---|---|---|---|
| D | Propylene Glycol & Diazolidinyl Urea (and) Methylparaben (and) Propylparaben Triethanolamine | 1.00 | 1.00 |
| | TOTAL | 100.0 | 100.0 |

*Emollient consisted of: IPJ 30% jojoba wax esters; 32% isopropyl esters; and 36% jojoba alcohols.

II. Combine Phase A and heat to 75° C., making sure all waxes melt and mixture is homogeneous. Then cool to 55° C.
III. Premix and heat Phase B to 45° C. with moderate agitation until all the Benzophenone-3 has dissolved.
IV. Add Phase B to Phase A with moderate agitation.
V. Heat water of Phase C to 65° C. Premix propylene glycol, methylparaben and propylparaben and add to heated water with agitation. Add sodium chloride. Mix 5–10 minutes, allowing sodium chloride to dissolve and mixture to cool to 55° C.
VI. Add Phase C slowly and continuously to Phase AB with moderate agitation. Maintain a creamy appearance by increasing agitation as mixture increases viscosity.
VII. Once combined allow to mix for 10–15 minutes and cool to 45° C.
VIII. Add Phase D with agitation and force cool to 30° C.
IX. One batch has cooled to 30° C., homogenize for approximately 10 minutes.
Observations The foregoing sunscreen products are water in oil emulsions. It was observed that product VI-A exhibited better spreadability and a smoother feel than product VI-B.

EXAMPLE VIII: LIPSTICK

A lipstick was prepared using the two special emollients of this invention.

| Phase | Ingredient | % wt./wt. |
|---|---|---|
| A. | Castor Oil | Q.S. |
| | Special emollient** | 5.0 |
| | Special emollient* | 7.5 |
| | Jojoba Esters-15 | 5.0 |
| | Jojoba Esters-70 | 1.0 |
| | Jojoba Oil | 2.5 |
| | Ceresin | 3.5 |
| | Ozokerite | 4.0 |
| | Microcrystalline Wax | 4.0 |
| | Polyparaben | 0.1 |
| | Silica | 0.2 |
| B. | Castor Oil | 13.0 |
| | Polyhydroxystearic Acid | 0.5 |
| | Titanium Dioxide | 5.5 |
| | Iron Oxides | 3.5 |
| | D & C Red No. 30 Talc Lake | 2.5 |
| | FD & C Blue No. 1 Aluminum Lake | 0.1 |
| | Iron Oxides | 0.8 |
| | Carmine | 0.2 |
| C. | Tocopherol | 0.1 |
| | TOTAL | 100.0 |

*Emollient consisted of: IPJ: 30% by weight jojoba wax esters; 32% isopropyl esters; and 36% jojoba alcohols.
**Emollient consisted of: HIPJ: 25% saturated jojoba wax esters; 37% saturated isopropyl esters; and 38% saturated jojoba alcohols.

I. Combine ingredients of Phase A and heat to 85° C. with moderate agitation.
II. Combine Phase B and pass 2 times through a 3-roll mill. Add Phase B to Phase A with propeller agitation.
III. Cool batch to 75° C., add Phase C and mix with propeller agitation. Fill as soon as possible.

Observations: The IPJ helps to wet and disperse the pigments (dries) in this lipstick, yielding a smoother, more even coverage to the lipstick. IPJ provides slip and gloss, and has no objectionable taste. HIPJ contributes to the wax matrix and strengthens the stick.

EXAMPLE IX: MASCARA

A mascara was prepared using the Special Emollient** of this invention.

| Phase | Ingredient | % wt./wt. |
|---|---|---|
| A. | Water | Q.S. |
| | Propylene Glycol | 3.0 |
| | Triethanolamine | 2.6 |
| B. | Acrylates/Octylacrylamide Copolymer | 4.0 |
| C. | Jojoba Esters 20 | 5.0 |
| | Carnauba Wax | 1.0 |
| | Candelilla Wax | 4.0 |
| | Synthetic Beeswax | 5.0 |
| | Special Emollient** | 3.0 |
| | Cetyl Alcohol | 3.0 |
| | Stearic Acid | 5.0 |
| | Tocopheryl Acetate | 0.2 |
| D. | Iron Oxides (and) Isopropyl Titanium Triisostearate | 11.0 |
| E. | Keratin Amino Acids | 0.1 |
| | Panthenol | 0.5 |
| | Preservative | Q.S. |
| | TOTAL | 100.0 |

**Emollient consists of: HIPJ: 25% saturated jojoba wax esters; 37% saturated isopropyl esters; and 38% saturated jojoba alcohols.

I. Heat water of Phase A to 90–95° C. and hold for 30 minutes. Begin cooling to 85–90° C. and add remaining ingredients in order listed with moderate propeller agitation.
II. Slowly sprinkle Phase B into Phase A at 85–90° C. with moderate propeller agitation. Mix for 30 minutes with propeller agitation at 85–90° C. (cover beaker to avoid water loss).
III. Combine Phase C and heat to 90° C. with moderate propeller agitation. When Phase C reaches 90° C., add Phase D (iron oxides) to Phase C with high shear homomixer agitation for 30 minutes.
IV. Add Phase CD slowly to AB at 85–90° C. with moderate propeller agitation. Mix 10 minutes. Force cool with propeller and sweep agitation to 50° C.
V. At 50° C., add Phase E in given order to Phase ABCD (batch) with sweep agitation for 20 minutes. Cool batch to 28–30° C. with sweep agitation.

Observations: This luxurious water-resistant mascara will add thickness and length to the eyelashes. The HIPJ helps to condition and thicken the lash, and contribute to the smooth, even application of this mascara to the eye lash.

EXAMPLE X: LIPBALM

A lipbalm wax prepared using the Special Emollient** of this invention.

| Phase | INCI Name | % wt./wt. |
|---|---|---|
| A. | Castor Oil | Q.S. |
| | Jojoba Esters | 13.000 |
| | Jojoba Esters | 6.500 |
| | Jojoba Esters (or) Hydrogenated | 1.000 |

-continued

| Phase | INCI Name | % wt./wt. |
|---|---|---|
| | Jojoba Oil | |
| | Carnauba Wax | 4.100 |
| | Candelilla (Euphorbia Cerifera) Wax | 5.100 |
| | Beeswax | 2.000 |
| | Special Emollient** | 3.000 |
| | Cetyl Ricinoleate | 2.000 |
| | Isopropylparaben (and) Isobutylparaben (and) Butylparaben | Q.S. |
| B. | Titanium Dioxide (and) Hybrid Sunflower (Helianthus Annuus) Oil | 3.000 |
| C. | Beta-Carotene | 0.003 |
| | Octyl Methoxycinnamate | 5.000 |
| | Tocopherol | 0.500 |
| | Flavor | 2.000 |
| | TOTAL | 100.000 |

*Emollient consisted of: HIPJ: 25% saturated jojoba wax esters; 37% saturated isopropyl esters; and 38% saturated jojoba alcohols.

I. Combine ingredients of Phase A and heat to 85° C. with moderate agitation.
II. Add Phase B to Phase A and mix with propeller agitation.
III. Cool batch to 75° C., add Phase C and mix with propeller agitation. Fill as soon as possible.

Observations: HIPJ forms an occlusive, emollient moisture barrier on the lips that helps keep them soft and supple when exposed to the elements (wind, sun, cold and dry heat). Each of the natural botanical emollients exhibits excellent oxidative stability. HIPJ contributes to the strength of the wax matrix.

The following list of cosmetic category codes identifies fields of use for the cosmetic emollient compositions and carriers of the present invention.

TABLE 1-2

FDA cosmetic category codes

01. Baby products.

A. Baby shampoos
B. Lotions, oils, powders and creams
C. Other baby products

02. Bath preparations

A. Bath oils, tablets and salts
B. Bubble Baths
C. Bath capsules
D. Other bath preparations 03. Eye makeup preparations A. Eyebrow pencil
B. Eyeliner
C. Eye shadow
D. Eye lotion
E. Eye makeup remover
F. Mascara
G. Other eye makeup preparations 04. Fragrance preparations A. Cologne and toilet waters
B. Perfumes
C. Powders (dusting and talcum, excluding aftershave talc)
D. Sachets
E. Other fragrance preparations 05. Hair preparations (non-coloring)

A. Hair conditioner
B. Hair spray (aerosol fixatives)
C. Hair straighteners
D. Permanent waves
E. Rinses (non-coloring)
F. Shampoos (non-coloring)

TABLE 1-2-continued

FDA cosmetic category codes

G. Tonics, dressings, and other hair grooming aids
H. Wave sets
I. Other hair preparations 06. Hair coloring preparations A. Hair dyes and colors (all types requiring caution statements and patch tests)
B. Hair tints
C. Hair rinses (coloring)
D. Hair shampoos (coloring)
E. Hair color sprays (aerosol)
F. Hair lighteners with color
G. Hair bleaches
H. Other hair coloring preparations 07. Makeup preparations (not eye)

A. Blushers (all types)
B. Face powders
C. Foundations
D. Leg and body paints
E. Lipstick
F. Makeup bases
G. Rouges
H. Makeup fixatives
I. Other makeup preparations 08. Manicuring preparations A. Basecoats and undercoats
B. Cuticle softeners
C. Hair creams and lotions
D. Nail extenders
E. Nail polish and enamel
F. Nail polish and enamel removers
G. Other manicuring preparations 09. Oral hygiene products A. Dentifrices (aerosol, liquid, pastes and powders)
B. Mouthwashes and breath fresheners (liquids and sprays)
C. Other oral hygiene products 10. Personal cleanliness A. Bar soaps and detergents
B. Deodorants (underarm)
C. Douches
D. Feminine hygiene deodorants
F. Other personal Cleanliness products 11. Shaving preparations A. Aftershave lotion
B. Beard softeners
C. Men's talcum
D. Preshave lotions (all types)
E. Shaving cream (aerosol, brushless and lather)
F. Shaving soap (cakes, sticks, etc.)
G. Other shaving preparations products 12. Skin care preparations (creams, lotions, powder and sprays)

A. Cleansing (cold creams, cleansing lotions, liquids and pads)
B. Depilatories
C. Face and neck (excluding shaving preparations)
D. Body and hand (excluding shaving preparations)
E. Foot powders and sprays
F. Moisturizing
G. Night
H. Paste masks (mud pacts)
I. Skin fresheners
J. Other skin products 13. Suntan preparations A. Suntan gels, creams and liquids
B. Indoor tanning preparations
C. Other suntan preparations

What is claimed:

1. An emollient composition comprising:

at least 10% by weight of fatty alcohols of the formula:

$R^1CH_2$—OH, at least 10% by weight of alkyl esters of the formula:

$R^1$—COO—$R^4$, and wax esters selected from the group consisting of:

$R^1$—COO—$CH_2$—$R^2$ and $R^2$—COO—$CH_2$—$R^1$, wherein $R^4$ is an alkyl or other aliphatic group, $R^1$ is $CH_3$—$(CH_2)_7$—CH=CH—$CH_2$—$(CH_2)_x$—, and $R^2$ is $CH_3$—$(CH_2)_y$ wherein x is 6, 8, 10 and 12, and y is 16, 18, 20 and 22.

2. The emollient composition of claim 1, wherein $R^4$ is $(CH_3)_2$—CH—.

3. The emollient composition of claim 1 wherein at least one $R^4$ comprises an isopropyl group.

4. An emollient carrier composition comprising:

partially saturated wax esters selected from the group consisting of:

$R^1$—COO—$CH_2$—$R^2$ and $R^2$—COO—$CH_2$—$R^1$, at least 10% by weight of alkyl esters comprising at least one material selected from the group consisting of:

$R^1$—COO—$CH_2$—$(CH_3)_2$ and $R^1$—COO—$R^4$, and fatty alcohols of the formula:

$R^1CH_2$—OH, wherein $R^4$ is an alkyl, a $C_nH_{2n+1}$, or other aliphatic group, $R^1$ is $CH_3$—$(CH_2)_7$—CH=CH—$CH_2$—$(CH_2)_x$—, and $R^2$ is $CH_3$—$(CH_2)_y$ wherein x is 6, 8, 10 and 12, and y is 16, 18, 20 and 22, and at least one additional ingredient selected form the group consisting of oils, fragrances, inorganic pigments, organic pigments, dyes, medicaments, antimicrobial agents, antibacterial agents, antifungal materials, anti-inflammatory agents, transcutaneously administered drugs, emulsifying agents, stabilizing agents, binders, fillers, antiagglomerants, ultraviolet radiation absorbers, insect repellants, pheromones, enzymes, and barrier materials.

5. The emollient carrier of claim 4 wherein $R^4$ is an alkyl, or a $C_nH_{2n+1}$ and wherein n is a positive integer.

6. The emollient carrier of claim 5 wherein at least one $R^4$ comprises an isopropyl group.

7. The emollient of claim 1 wherein said fatty alcohol comprises at least 33% by weight of said emollient carrier.

8. The emollient of claim 1 wherein said wax ester comprises at least 33% by weight of said emollient carrier.

9. The emollient of claim 1 wherein said alkyl ester comprises at least 33% by weight of said emollient carrier.

10. A cosmetic composition comprising the emollient carrier of claim 4 wherein pigment comprises at least 0.1% by total weight of said cosmetic composition.

11. A cosmetic composition comprising the emollient carrier of claim 5 wherein pigment comprises at least 0.1% by total weight of said cosmetic composition.

12. A cosmetic composition comprising the emollient carrier of claim 6 wherein pigment comprises at least 0.1% by total weight of said cosmetic composition.

13. A cosmetic product containing the emollient of claim 1.

14. A topically applied pharmaceutical product containing the emollient of claim 1.

15. The emollient composition of claim 1 further comprising at least one compound selected from the group consisting of:

$R^2CH_2$—OH and $R_2$—COO—$R_4$, wherein $R_2$ and $R_4$ are as defined above.

16. The emollient carrier composition of claim 4 further comprising at least one compound selected from the group consisting of:

$R^2CH_2$—OH and $R_2$—COO—$R_4$, wherein $R_2$ and $R_4$ are as defined above.

* * * * *